United States Patent
Prosl

(10) Patent No.: US 9,339,036 B2
(45) Date of Patent: May 17, 2016

(54) ANTIMICROBIAL LOCKING SOLUTIONS COMPRISING TAURINAMIDE DERIVATIVES AND BIOLOGICALLY ACCEPTABLE SALTS AND ACIDS, WITH THE ADDITION OF SMALL CONCENTRATIONS OF HEPARIN

(71) Applicant: ND Partners, LLC, Boston, MA (US)

(72) Inventor: Frank R. Prosl, Duxbury, MA (US)

(73) Assignee: ND Partners, LLC, Boston, MA (US)

( * ) Notice: Subject to any disclaimer, the term of this patent is extended or adjusted under 35 U.S.C. 154(b) by 0 days.

(21) Appl. No.: 14/034,877

(22) Filed: Sep. 24, 2013

(65) Prior Publication Data

US 2014/0243323 A1 Aug. 28, 2014

Related U.S. Application Data

(63) Continuation of application No. 13/199,605, filed on Sep. 2, 2011, now Pat. No. 8,541,393, which is a continuation of application No. 12/661,183, filed on Mar. 11, 2010, now abandoned, which is a continuation of application No. 10/979,547, filed on Nov. 2, 2004, now Pat. No. 7,696,182.

(51) Int. Cl.
| | |
|---|---|
| *C07D 407/04* | (2006.01) |
| *C07H 19/044* | (2006.01) |
| *A01N 43/88* | (2006.01) |
| *A61K 31/18* | (2006.01) |
| *A61K 31/185* | (2006.01) |
| *A61K 31/727* | (2006.01) |
| *A01N 25/02* | (2006.01) |

(52) U.S. Cl.
CPC ............... *A01N 43/88* (2013.01); *A01N 25/02* (2013.01); *A61K 31/18* (2013.01); *A61K 31/185* (2013.01); *A61K 31/727* (2013.01)

(58) Field of Classification Search
CPC ... A61K 31/727; A61K 31/549; A61K 31/54; C08B 37/0075; C07D 285/16
USPC ...................... 514/56, 222.5, 223.5, 553, 602
See application file for complete search history.

(56) References Cited

U.S. PATENT DOCUMENTS

| | | | |
|---|---|---|---|
| 4,096,241 A | 6/1978 | Geistlich et al. | |
| 4,107,305 A | 8/1978 | Pfirrmann | |
| 4,337,251 A | 6/1982 | Pfirrmann | |
| 4,587,268 A | 5/1986 | Pfirrmann | |
| 4,587,284 A | 5/1986 | Luissi et al. | |
| 4,604,391 A | 8/1986 | Pfirrmann | |
| 4,626,536 A | 12/1986 | Pfirrmann | |
| 4,654,338 A | 3/1987 | Jones et al. | |
| 4,772,468 A | 9/1988 | Pfirrmann | |
| 4,797,282 A | 1/1989 | Wahlig et al. | |
| 4,853,225 A | 8/1989 | Wahlig et al. | |
| 4,882,149 A | 11/1989 | Spector | |
| 4,905,700 A | 3/1990 | Wokalek et al. | |
| 4,960,415 A | 10/1990 | Reinmuller | |
| 4,980,374 A | 12/1990 | Steudle et al. | |
| 5,032,615 A | 7/1991 | Ward et al. | |
| 5,077,281 A | 12/1991 | Reinmuller | |
| 5,167,961 A | 12/1992 | Lussi et al. | |
| 5,210,083 A | 5/1993 | Pfirrmann | |
| 5,362,754 A | 11/1994 | Raad et al. | |
| 5,417,675 A | 5/1995 | Watanabe et al. | |
| 5,417,975 A | 5/1995 | Lussi et al. | |
| 5,573,771 A | 11/1996 | Geistlich et al. | |
| 5,593,665 A | 1/1997 | Pfirrmann et al. | |
| 5,603,921 A | 2/1997 | Bowen | |
| 5,688,516 A | 11/1997 | Raad et al. | |
| 5,725,553 A | 3/1998 | Moenning | |
| 5,889,183 A | 3/1999 | Herdeis et al. | |
| 5,899,874 A | 5/1999 | Jonsson | |
| 5,954,691 A | 9/1999 | Prosl | |
| 6,166,007 A | 12/2000 | Sodemann | |
| 6,174,537 B1 | 1/2001 | Khan | |
| 6,258,797 B1 | 7/2001 | Lehner | |
| 6,350,251 B1 * | 2/2002 | Prosl et al. ................. | 604/93.01 |
| 6,423,706 B2 | 7/2002 | Sodemann | |
| 6,447,488 B2 | 9/2002 | Estabrook et al. | |
| 6,498,157 B2 | 12/2002 | Sodemann | |
| 6,569,852 B1 | 5/2003 | Sodemann | |
| 6,685,694 B2 * | 2/2004 | Finch et al. .................. | 604/508 |
| 7,696,182 B2 * | 4/2010 | Prosl ............................... | 514/56 |

(Continued)

FOREIGN PATENT DOCUMENTS

| | | |
|---|---|---|
| DE | 4137544 | 5/1993 |
| EP | 0 698 398 | 2/1996 |
| EP | 1 245 247 | 10/2002 |

(Continued)

OTHER PUBLICATIONS

Elliot, T.S.J. et al., Effects of Heparin and Chlorbutol on Bacterial Colonisation of Intravascular Cannulae in an in Vitro Model, Journal of Hospital infection, 1989, pp. 193-200, 14.

(Continued)

*Primary Examiner* — Ganapathy Krishnan

(74) *Attorney, Agent, or Firm* — Pandiscio & Pandiscio

(57) ABSTRACT

The present invention relates to inhibiting or preventing infection and protecting against patency complications after a blood catheter has been inserted in a patient comprising administering to the device a pharmaceutically effective amount of a composition comprising (A) at least one taurinamide derivative, and (B) heparin at a low concentration.

20 Claims, No Drawings

(56) References Cited

U.S. PATENT DOCUMENTS

| | | | |
|---|---|---|---|
| 8,541,393 B2* | 9/2013 | Prosl | 514/56 |
| 2003/0225066 A1 | 12/2003 | Polaschegg | |

FOREIGN PATENT DOCUMENTS

| | | |
|---|---|---|
| EP | 1 327 453 | 7/2003 |
| GB | 1 124 285 | 8/1968 |
| JP | 63-500943 | 4/1988 |
| WO | WO 94/03174 | 2/1994 |
| WO | WO 97/25052 | 7/1997 |
| WO | WO 98/28027 | 7/1998 |
| WO | WO 00/01391 | 1/2000 |
| WO | WO 00/10385 | 3/2000 |
| WO | WO 01/52926 | 7/2001 |
| WO | WO 2006/050161 | 5/2006 |

OTHER PUBLICATIONS

Cowan, C.E., Antibiotic Lock Technique, Journal of Intravenous Nursing, 1992, pp. 283-287, vol. 15, No. 5.

Mochizuki, M. et al., Modification of Central Veneous Catheter Flush Solution Improves In Vitro Antimicrobial Activity, The Journal of Infectious Diseases, 1992, pp. 944-945.

Preliminary Results Treating Persistent Central Venous Catheter infections with the Antibiotic Lock Technique in Pediatric Patients, The Pediatric infectious Disease Journal, 1994, pp. 903-931, vol. 13, No, 10.

Allon, Michael, Prophylaxis against Dialysis Catheter-Related Bacteremia with a Novel Antimicrobial Lock Solution, Clinical Infectious Diseases, 2003, pp. 1539-1544.

ASAIO Renal Abstract, ASAIO Journal, 2009, cover page and p. 178.

Betjes, M.G.H. et al., Prevention of dialysis catheter-related sepsis with a citrate-taurolidine-containing lock solution, Nephrology Dialysis Transplantation, 2004, pp. 1-6.

Macrae, J.M., Citrate 4% versus Heparin and the Reduction of Thrombosis Study (CHARTS), Clinical Journal of the American Society of Nephrology, 2008, pp. 369-374.

Nori, U.S. et al., Comparison of Low-Dose Gentamicin With Minocycline as Catheter Lock Solutions in the Prevention of Catheter-Related Bacteremia, American Journal of Kidney Diseases, 2006, pp. 596-605.

Polaschegg, H.D., Loss of Catheter Locking Solution Caused by Fluid Density, ASAIO, 2005, pp. 230-235.

Polaschegg, H.D., Physics of Catheter Locking Solutions, Dialysis Times, 2005, pp. 1-6.

Quarello, F. et al., Prevention of Hemodialysis Catheter-Related Bloodstream Infection Using an Antimicrobial Lock, Blood Purification, 2002, pp. 87-92.

Taylor, C. et al., A New Hemodialysis Catheter-Locking Agent Reduces Infections in Haemodialysis Patients, Journal of Renal Care, 2008, pp. 116-120.

Weijmer, M.C. et al., Randomized, Clinical Trial Comparison of Trisodium Citrate 30% and Heparin as Catheter-Locking Solution in Hemodialysis Patients, Journal of the American Society of Nephrology, 2005, pp. 2769-2777.

Yevzlin, A.S. et al., Concentrated Heparin Lock Is Associated with Major Bleeding Complications after Tunneled Hemodialysis Catheter Placement, Seminars in Dialysis, 2007, pp. 351-354.

Moran, J.E. et al., Locking Solutions for Hemodialysis Catheters; Heparin and Citrate—A Position Paper by ASDIN, 2008, pp. 1-3.

Braumann, C. et al., Influence of intraperitoneal and systemic application of taurolidine and taurolidine/heparin during laparoscopy on intraperitoneal and subcutaneous tumour growth in rats, Clinical & Experimental Metastasis, 2001, 547-552.

McIntyre et al., Locking of tunneled hemodialysis catheters with gentamicin and heparin, Kidney International, 2004, pp. 801-805, vol. 66.

Allon, Michael, Prophylaxis Against Dialysis Catheter-Related Bacteremia: A Glimmer of Hope, Feb. 2008, pp. 165-168, vol. 51, No. 2.

Beathard, Gerald A. et al., Infection Associated with Tunneled Hemodialysis Catheters, Seminars in Dialysis, 2008, pp. 528-538, vol. 21, No. 6.

Droste, Jan C. et al., Stability and in-vitro efficacy of antibiotic-heparin lock solutions potentially useful for treatment of central venous catheter-related sepsis, Journal of Antimicrobial Chemotherapy, 2003, pp. 849-855.

Jurewitsch, Brian et al., Taurolidine 2% as an Antimicrobial Lock Solution for Prevention of Recurrent Catheter-Related Bloodstream Infections, Journal of Parenteral and Enteral Nutrition, 1998, vol. 22, No. 4.

Polaschegg, Hans-Dietrich et al., Overspill of Catheter Locking Solution: Safety and Efficacy Aspects, ASAIO Journal, 2003.

Root, Jennifer L. et al., Inhibitory Effect of Disodium EDTA upon the Growth of Staphylococcus epidermis In Vitro: Relation to infection Prophylaxis of Hickman Catheters, Antimicrobial Agents and Chemotherapy, Nov. 1988, pp. 1627-1631. vol. 32, No. 11.

Simon, Arnie et al., Taurolidine-citrate lock solution (TauroLock) significantly reduces CVAD-associated grampositive infections in pediatric cancer patients, BMC Infectious Diseases, Jul. 29, 2008.

Sodemann, Klaus et al., Two Years' Experience with Dialock and CLS (A New Antimicrobial Lock Solution), Blood Purification, 2001.

Blenkharn, J. I., The Antimicrobial Activity of Taurolin—A possible Additive for Parenteral Nutrition Solutions, Clinical Nutrition, 1987.

Darouiche, Rabih O. et al., Prevention of Catheter-Related Infections: The Skin, Nutrition, 1997, vol. 13, No. 4(suppl).

Flanigan, Michael J. et al., Regional Hemodialysis Anticoagulation: Hypertonic Tri-Sodium Citrate or Anticoagulant Citrate Dextrose-A, American Journal of Kidney Diseases, Apr. 1996, pp. 519-524. vol. 27, No. 4.

Gorman, S. P. et al., A Compartive Study of the Microbial Anti-Adherence Capacities of Three Antimicrobial Agents, Journal of Clinical Pharmacy and Therapeutics, 1987.

Johnston, D.A. et al., Taurolin for the prevention of parenteral nutrition related infection: antimicrobial activity and long-term use, Clinical Nutrition, 1993.

Jones. D.S. et al., The effects of three non-antibiotic, antimicrobial agents on the surface hydrophobicity of certain micro-organisms evaluated by different methods, Journal of Applied Bacteriology, 1991.

Myers, Evelyn et al., The Relationship between Structure and Activity of Taurolin, Journal of Applied Bacteriology, 1980.

Traub, Walter H. et al., Taurolidine: in vitro Activity against Multiple-Antibiotic-Resistant, Nosocomially Significant Clinical Isolates of Staphylococcus aureus, Enterococcus faecium, and Diverse Enterobacteriaceae, Chemotherapy, 1993.

Wanten, G.J. et al., Taurolidine Versus Heparin Lock to Prevent Catheter-Related Bloodstream infections (CRBSI) in Patients on Home Parenteral Nutrition, A Prospective Randomized Trial, Clinical Nutrition Supplements, 2008.

Willatts, Sheila M. et al., Effect of the antiendotoxic agent, taurolidine, in the treatment of sepsis syndrome: A placebo-controlled, double-blind trial, Critical Care Medicine, Jun. 1995, pp. 1033-1039, vol. 23, Issue 6.

Kirsch, Lee E. et al., The Effect of Polyvinylpyrrolidine on the Stability of Taurolidine, Pharmaceutical Development and Technology, 1997.

* cited by examiner

ANTIMICROBIAL LOCKING SOLUTIONS COMPRISING TAURINAMIDE DERIVATIVES AND BIOLOGICALLY ACCEPTABLE SALTS AND ACIDS, WITH THE ADDITION OF SMALL CONCENTRATIONS OF HEPARIN

REFERENCE TO PENDING PRIOR PATENT APPLICATIONS

This patent application is a continuation of pending prior U.S. patent application Ser. No. 13/199,605 filed Sep. 2, 2011 by Frank R. Prosl for ANTIMICROBIAL LOCKING SOLUTIONS COMPRISING TAURINAMIDE DERIVATIVES AND BIOLOGICALLY ACCEPTABLE SALTS AND ACIDS, WITH THE ADDITION OF SMALL CONCENTRATIONS OF HEPARIN which is in turn a continuation of prior U.S. patent application Ser. No. 12/661,183, filed Mar. 11, 2010 by Frank R. Prosl for ANTIMICROBIAL LOCKING SOLUTIONS COMPRISING TAURINAMIDE DERIVATIVES AND BIOLOGICALLY ACCEPTABLE SALTS AND ACIDS, WITH THE ADDITION OF SMALL CONCENTRATIONS OF HEPARIN which is in turn a continuation of prior U.S. patent application Ser. No. 10/979,547, filed Nov. 2, 2004 by Frank R. Prosl ANTIMICROBIAL LOCKING SOLUTIONS COMPRISING TAURINAMIDE DERIVATIVES AND BIOLOGICALLY ACCEPTABLE SALTS AND ACIDS, WITH THE ADDITION OF SMALL CONCENTRATIONS OF HEPARIN.

The above-identified patent applications are hereby incorporated herein by reference.

FIELD OF THE INVENTION

The present invention relates to an improved composition for preventing infection and clotting in hemodialysis catheters. The invention further relates to an improved composition for maintaining patency of indwelling catheters involved in central blood access.

BACKGROUND OF THE INVENTION

Hemodialysis access systems for access to a patient's vascular system for exchange of blood between the vascular system and an external processing apparatus are well known in the art. The simplest such system is a catheter alone placed directly in the patient's right jugular vein with the distal end extending into the central venous system, typically into the superior vena cava. Other more complicated systems, for example ports, usually involve indwelling catheters as well. The exchange of blood for hemodialysis treatment typically involves high blood flow rates under conditions designed not to induce shear stress beyond a certain level so as to not cause red cell damage or the activation of platelets.

As with any implanted device, placement of an object that must remain in the patient over a protracted period of time gives rise to the likelihood of blood stream infection promoted by the indwelling device. Infection risk is seriously aggravated by the fact that such devices are frequently handled and manipulated by medical workers, leading to microbial colonization of the catheter's internal surfaces, that is, formation of a biofilm in the lumen. Infection from a biofilm reservoir is much more serious than a simple infection, since it is often impossible to eradicate with conventional means. In refractory cases the device must be explanted to treat the patient effectively. As a result, the literature, both scientific and patent, is replete with hopeful but not definitive suggestions as to how to defeat, or at least hold at bay, catheter related infections.

In describing approaches to preventing or treating catheter infections, authors and practitioners generally refer to "locking" the catheter, but also sometimes use the term "flushing" the catheter. Usage in the case of the term "flushing" is ambiguous, and therefore some explanation of terminology is necessary. With respect to implanted catheters, authors and practitioners typically speak of "locking" a catheter between uses. In this context, "locking" means filling the catheter lumen with a substance that is biocidal or an anticoagulant but preferably both, followed by leaving it there until the catheter has to be used again. (Typically, "locking" a catheter with a given solution also includes in the assumed procedure the follow up event of withdrawing the solution from the catheter before using, for example, a syringe to suck the solution out of the catheter whenever the catheter must be used again.) For example, in the past authors or practitioners have spoken of heparin as a catheter lock. That word usage is relatively unambiguous.

Authors and practitioners have, however, not used the terms "flush" and "flushing" unambiguously. Much of the time "flushing" has a meaning that is familiar to non-experts, namely sending a fluid through the catheter or into it and quickly back out again as a kind of washing. However, a substantial fraction of authors and practitioners also use the terms "flush" and "flushing" as synonymous with "lock" and "locking" as defined above, that is, meaning putting a solution in a catheter and leaving it there for an extended period and then taking it out when the practitioner wants to use infuse the patient or remove fluid from the patient. In this application the former meaning of "flush" and "flushing" is generally intended. However, in reviewing the literature the other usage must be borne in mind.

Antibiotics have been used to treat devices such as catheters to prevent infection, but chronic use of antibiotics as a prophylactic accelerates emergence of antibiotic-resistant bacterial strains. Advances in catheter locks described in the scientific literature and other patent documents have involved the use of a substance generally referred to as taurolidine and/or taurinamide and taurinamide derivatives for routine antimicrobial use, in particular in catheters. Taurolidine and related compounds are biocidal but are known not to induce development of resistant bacterial strains. For example, Sodemann U.S. Pat. No. 6,166,007, issued Dec. 26, 2000 and Sodemann, U.S. Pat. No. 6,423,706, issued Jul. 23, 2002, among others, disclosed use of taurolidine and other taurinamide-related compounds as part of a catheter lock solution.

Coagulation of the blood inside catheters in or connected to the vascular system has also proven troublesome and many methods have been tried for its prevention, particularly for inhibiting the clogging of the catheter, which can diminish or destroy the catheter's usefulness. It is standard procedure to flush blood from the catheters and then lock them with a heavy-duty anticoagulant, heparin locking solution being the standard. Unfortunately heparin alone lacks biocidal capability, but this deficiency is often ignored.

Current indwelling blood catheter maintenance practices, particularly with respect to hemodialysis catheters, have evolved to the point where current de facto practices require that an extremely high concentration heparin be instilled as a lock between uses. Normally the heparin lock concentration is 5,000 units per ml. By comparison, therapeutic levels in the blood to prevent clotting in patients with disorders whereby their blood to form clots are generally in the range of 0.2 to 0.4 units per ml. It is also known that blood used in laboratory experiments can be maintained in a fluid state (i.e., not clotted) by using a heparin concentration in the range of 5 units or so.

Unfortunately, and contrary to good catheter locking practice, sometimes medical personnel flush heparin—in the flow-through sense—from the catheter directly into the patient instead of drawing it out, e.g., with a syringe. Such events may be accidental or even in some cases deliberate when the practitioner is attempting to unblock a clotted catheter. An important consideration in the use of heparin is that if too much heparin is pushed into the patient's vascular system the patient may become systemically anticoagulated, creating a significant risk to the patient bleeding out, that is, dying of uncontrollable hemorrhage. Further, some patients are allergic in heparin. For both reasons, minimizing systemic administration of heparin is important.

U.S. Pat. Nos. 6,166,007 and 6,423,706, cited above, disclosed solutions based on taurinamide derivatives, preferably taurolidine, combined with biologically benign salts and corresponding acids, most preferably citrate salts along with citric acid, as catheter locking solutions and solutions for maintaining implants having both antimicrobial and anticoagulant properties. Selection of optimum concentrations of these substances while also controlling the pH of the solution to be generally slightly acidic increases the antimicrobial efficacy of taurolidine in solution.

Other substances could be used as anticoagulants, for example EDTA, enoxaparin sodium, coumarin, indanedione derivative, anisindione, warfarin protamine sulfate, streptokinase, urokinase, and others. However, the properties of citrate and citric acid in a proper pH balance give special effectiveness to catheter locks of the referenced lamination.

It has been empirically found in practicing the above-referenced patents, however, that sometimes taurolidine reacts with a patient's red blood cells inside the catheter and changes the characteristics of the blood clot that normally forms at the distal end of the catheter. This change sometimes results in clot fragments or nuclei remaining attached to the interior luminal surface of the catheter after the lock solution is withdrawn in preparation for catheter use. The end result of even a small clot fragment attached to the inside of a catheter is at least partial obstruction of flow through the catheter. In the case of hemodialysis catheters, this causes a significant increase in resistance to blood flow in the catheter. Too high a resistance increase may cause blood damage and can also reach an upper limit that requires a reduction in blood flow rate. Such flow resistance interferes with dialysis efficiency and extends dialysis time of treatment.

The formulation of taurolidine with citrate and citric acid described in U.S. Pat. Nos. 6,166,007 and 6,423,706, cited above, has worked well in minimizing catheter-caused infections in hemodialysis patients. Dr. Sodemann, conducted initial trials of these compositions including evaluation of pH values for maximizing the antimicrobial properties of the composition.

Dr. Sodemann and others also performed clinical trials of the final compositions in Europe to obtain approval for commercialization there. The data from Europe demonstrated nearly complete elimination of catheter related bloodstream infection, compared to the rate observed with heparin locks and simultaneous achievement of a catheter potency rate (the inverse of the rate of complications due to blood flow resistance during hemodialysis) comparable to that of heparin lock solutions.

Subsequently, in 2001 and 2002, however, the university of Alabama Medical Center conducted a hemodialysis clinical trial using the Sodemann taurolidine lock formulation. The clinical results confirmed the low infection rate with the taurolidine based lock solution. However, this trial experienced a high rate of catheter patency complications compared with the heparin lock control group. Allon, M., "Prophylaxis against dialysis catheter-related bacteremia with a novel antimicrobial lock solution." *Clinical Infec. Dis.* 2003(June) 15; 36 (12): 1539-44.

The usual intervention to correct observed high flow resistance in a hemodialysis catheter is a clot-lysing procedure, which cleans out the catheter. Whenever the University of Alabama practitioners experienced a patency complication, they would perform the clot lysing procedure, which was rapid and 100% successful. This result suggested that the flow resistance was caused by internal adhesion to the catheter. The calculation of catheter patency complication intervention in the University of Alabama study was determined by taking the number of lysing procedures performed during the study period and dividing it by the sum of patient days in the trial. The patency complication rate for the group receiving the taurolidine-based locking solution was approximately 4 times higher than for the heparin lock group.

In hemodialysis, blood is withdrawn from the patient via a catheter lumen with its tip in a major blood supply. The blood enters a machine which removes toxins and water from the blood. In U.S. hemodialysis practice, unlike European practice, the blood flow rate is higher and typically approximately 400 ml/min. In order not to damage blood cells at this flow rate, practitioners monitor the flow resistance in the catheter and if the resistance increases above an alarm setting the operator must clear the catheter or slow down the flow. (Lower flow rate is necessary in such situations because the combination of high flow rates and obstructions creates eddies and other non-laminar flow conditions that create shear forces that damage blood cells.) However, slower flow rates require a considerable increase in the time of dialysis to achieve the same level of toxin removal, lengthening the time necessary for an effective hemodialysis session. Longer sessions lower both patient acceptance and clinic productivity.

Several differences in medical practice between the European trials and the U.S. trials probably contributed to the difference in result. Especially significant was that higher blood flow rates are set during dialysis in the U.S. and a different catheter was used in the U.S. clinical trials.

In addition, careful observation taught that, after instillation of a lock solution into a catheter, a small amount of lock solution flows out of the catheter into the patient's vascular system. The lost catheter lock is replaced by blood in the distal tip region of the catheter. This phenomenon is described by Polaschegg, published U.S. Patent Application No. 2004/0156908 A1 paragraphs [0022], [0026]. Polaschegg further describes at paragraphs [0026] to [0027] a related observation, systemic anticoagulation in patients due to transfer of heparin locking solution. This observation has also been reported in medical journals, e.g., as cited in Polaschegg paragraph [0026].

Blood that enters the distal tip portion of the catheter by virtue of being interchanged with locking solution quickly becomes stagnant and therefore typically forms a clot inside the catheter near the distal tip, notwithstanding the presence of high-concentration heparin in the catheter. In hemodialysis catheters and other catheters in the vascular system, the clot that forms in the distal tip portion is withdrawn during conventional preparatory steps prior to initiating, for example, a hemodialysis session. These preparatory steps are the withdrawal of the lock solution, followed by a back flush with a small amount of saline to clear any residual blood or lock in the catheter. The withdrawn material (the lock solution, the clot and some blood) is sucked into a syringe and is discarded.

However, efforts to withdraw the intra-luminal clot are not always effective. Even in current practice, potency complications still occur at a relatively high rate even with high concentration heparin. Any blood clot or clot fragment adhering to the luminal surface of a catheter increases blood flow resistance during treatment, especially at the high blood flows typical of American hemodialysis. Established practices in hemodialysis clinics set a maximum allowable flow resistance in the blood flow path, inferred from increased pressures and decreased flow rates, that must not be exceeded as this may cause damage to red cells and may activate platelets, triggering a clotting response. Consequently, alarms are incorporated in hemodialysis machines to warn the nurse when, e.g., pressure levels are exceeded. Corrective action options are limited and mainly consist of slowing the blood flow rate or stopping the session and performing a catheter clot lysing procedure to open up the catheters to restore patency. In either case, the interventions are a major inconvenience to the patient and diminish the operational efficiency of the hemodialysis clinic.

The trial results by Dr Allon were examined by researchers in a group of experiments at the Naval Blood Laboratory and Boston University Medical School. These experiments determined that blood in contact with high concentration taurolidine solution (such as occurs at the interface between blood and taurolidine locking solution in a catheter) underwent changes, including morphological changes to red cells that did not happen with exposure to just heparin. However, the researchers were not able to determine exactly how their results were relevant to the findings in the University of Alabama clinical trial.

Additional experiments were undertaken seeking to determine scientifically the reasons for the different results. This work comprised in vitro experiments with modifications to the taurolidine-based lock formulation. Testing was done with fresh human blood using silicone rubber catheters commonly used in U.S. hemodialysis practice. Catheter lock and later blood test articles were subjected to conditions simulating as much as possible the environment that occurs in in vivo hemodialysis. Several catheters were tested simultaneously.

Test catheters were mounted in a vertical orientation and filled with various lock solution formulations. The distal tip was placed in a beaker containing fresh blood and blood was pulled into the catheter for a distance of about 3 centimeters. The distal tip and the proximal tip of each catheter were clamped shut. The distal portion of the catheter was immersed in saline at 99° F. for 3 days. This time period was comparable to the longest quiescent time period between live hemodialysis sessions. Test specimens included a conventional heparin lock, taurolidine based locks at various pH conditions, and taurolidine locks with and without PVP additives.

The catheter contents were observed visually during the three day time periods. The catheters themselves were translucent and the material holding the saline and the catheter allowed easy visual observation.

The first test sequence used the taurolidine lock in commercial use in Europe and a conventional heparin lock at 5,000 units per ml. It was observed that the high concentration heparin lock behaved very differently with respect to clotting compared to the taurolidine formulation. With respect to the heparin lock, clotting of the blood in the catheter started on the end of the blood segment away from the blood-catheter lock interlace. With the taurolidine based catheter lock, the blood started clotting right at the blood-catheter lock interface. In addition, the distal end clot was different in color. The clot formed with the heparin lock was reddish brown, but the clot formed with the taurolidine-based lock solution was black, suggesting the formation of met-hemoglobin. The presence of met-hemoglobin suggests damage to red blood cells by some agent.

Tests were also performed to simulate the procedure that occurs in preparation for hemodialysis session. In a hemodialysis clinic, a nurse withdraws the lock solution from the catheter with a syringe and the catheter is flushed with 10 ml of saline prior to the hook up to the hemodialysis machine. In the in vitro study referred to above, at the end of the 3 day quiescent period, is syringe was attached to the proximal end of the catheter and the clamp on the distal end was removed. The distal tip was then immersed in saline. A syringe was used to withdraw the catheter contents.

It was noted that the clot in the heparin based locking solution could be easily removed intact from the catheter while the clot in the taurolidine based experiments fragmented easily and crumbled. (One test in which the pH of the taurolidine-based locking solution was raised to 6 resulted in less met-hemoglobin in the distal end clot but did not completely solve the problem.) The solidity and mechanical strength of the clots were qualitatively compared by compressing them with a small rod. It was observed that the heparin clot was resilient and similar to the behavior of soft rubber while the clot formed in the taurolidine-based locking solution did not have any resiliency and broke apart easily.

Also, in the catheters containing the taurolidine-based locking solution the procedure often did not completely remove the clot at the distal end. When the clot broke up, fragments remained adhered to the lumen surface of the catheter. Subsequently, in a like manner to the actual clinical situation, the catheter was flushed vigorously with a 10 ml saline solution to determine if the clot fragment attachment could be broken away. This flushing action did not usually dislodge the adhered fragments. In summary, the clot in the catheters containing the heparin locking solution disengaged easily and completely, while the clot in the catheters containing the taurolidine-based locking solution fragmented, with portions remaining stuck to the catheter lumen even after the flush procedure.

These tests comparing the heparin locking solution with a taurolidine-based locking solution suggested that the patency problems experienced in the U.S. clinical trial at the University of Alabama were explained by difference in the nature of the clot formed at the distal end of the catheter with different locking solutions. During the Naval Blood Laboratory/Boston University Medical School experiments referred to above, it was determined that, with one exception, modifications of the taurolidine formulation did not affect the character of the distal tip clot. It was determined that the addition of very low concentrations of heparin (final concentration about 100 units per ml) to the taurolidine formulation minimized or eliminated the evidently taurolidine-induced changes to the character of the clots.

Based on this result, in vitro experiments were also undertaken with a low concentration of heparin added to a test specimen of the standard taurolidine formulation. This solution formulation was also subjected to simulated conditions during the simulated quiescent period. The resulting observation was that the distal tip clot was able to be completely removed intact just as if high concentrations of heparin had been used and its mechanical properties and appearance were similar to the high heparin concentration samples.

However, heparin is a dangerous substance demanding respect. It is usually given systemically to patients who are suffering dangerous disorders involving clotting, such as acute thrombo-embolism, unstable angina, and active thrombosis, which are life threatening or cause severe harm. Common complications of heparin administration are internal bleeding and heparin allergy, which can manifest in severe system clotting. In any patient, too high a level of heparin will cause hemorrhaging. For hemodialysis patients, however, bleeding is a special problem, since many such patients have a reduced tendency to clot. It is an object of the current invention to provide a level of heparin addition to taurolidine-based catheter lock solutions that will eliminate or minimize the danger that heparin infused into a patient will prompt uncontrolled bleeding.

SUMMARY OF THE INVENTION

The present invention provides a improvement to Taurolidine based antimicrobial and anti-coagulant lock solutions by reducing catheter patency complications brought on by taurolidine reacting with red cells and the characteristics of the clot formed in the distal portion of a catheter. The clot that forms in the presence of taurolidine has a tendency to adhere to the inside surfaces of the hemodialysis catheter lumen and thereby produce high flow resistance which interferes with the hemodialysis treatment in some circumstances. These lock solutions comprise pharmaceutically effective amounts or concentrations of: at least one taurinamide derivative, at least one compound selected from the group consisting of biologically acceptable acids and biologically acceptable salts thereof, and heparin in small amounts and concentrations insufficient by itself to provide protection of a hemodialysis catheter against loss of patency but sufficient to prevent formation of clot fragments which adhere to the luminal surfaces of the hemodialysis catheter and resist removal.

In summary, investigators solved a problem that was first discovered during the commercialization of a new potent prophylactic which protects against catheter infections. It was learned that under certain circumstances, taurolidine and other taurinamide derivatives can react with blood, ultimately causing a patency complication in hemodialysis catheters. Experiments were conducted both on the bench and in clinical trials to elucidate the nature of the problem and an unexpected solution was revealed, namely, adding low-concentration heparin to the taurolidine formulation. Heparin is added in an amount too small to actually protect hemodialysis catheters from bulk clotting, but in amounts it was able to protect blood in a way that normal clotting processes did not produce clots with a tendency to stick to catheter walls.

DESCRIPTION OF THE PREFERRED EMBODIMENTS

The most preferred embodiment of the invention is a combination of a taurolidine or taurultam based antibacterial solution in combination with an anticoagulant and/or calcium chelating substance such as citrate also in solution, the solution having a pH that maximizes the antimicrobial activity of the taurolidine, with a low concentration of heparin, said concentration being so low that the threat of systemic anticoagulation of the patient is minimized or eliminated.

The therapeutic heparin concentration in the systemic circulation even in patients with severe clotting tendencies rarely exceeds 1 unit/ml over the entire blood stream. More typically, concentrations are maintained in the range of 0.2 units per ml of blood to 0.4 units per ml of blood.

Hemodialysis patients, on the other hand, more typically have low platelet counts and other blood deficiencies that inhibit clotting rather than promote it. Thus the upper limit for blood concentration should be conservative. The current invention assumes that 0.5 units heparin per ml of blood, in the total blood supply, is a safe upper limit for prevention of adverse consequences from infusing heparin into a patient's blood stream. However, the preferred upper limit would be based on the minimum value typically cited for antithrombotic effect, namely the 0.2 units per ml of blood cited above.

Various means exist for estimating total blood volume for patients. The inventor herein used the following formulas:

For men:

$$V_B = 0.3669 \times (H)^1 + 0.03219 \times W + 0.604$$

For women:

$$V_B = 0.3561 \times (H)^1 + 0.03308 \times W + 0.1833.$$

Where H is patient height in meters and W is patient total body weight in kilograms. The resulting blood volume is in liters (multiplied by 1000 to obtain volume in ml). Using test values for typical patients, a range of blood volumes of 5000 to 6000 ml for males, 4000 to 5000 ml for females, is obtained. A mid-range value of 5000 ml is used in the calculations that follow, but the wide variability from gender to gender and from patient to patient should be kept in mind.

A typical hemodialysis catheter volume is approximately 3 ml. Typical unavoidable spillage of catheter lock solution into the patient is about ⅓ of that value, or 1 ml. If the concentration of heparin in the catheter lock solution is $L_{concentration}$, loss of that much heparin into the patient would produce a vascular concentration of ($L_{concentration}$) (spilled catheter volume)=(blood concentration)×(blood volume) (where, in the most routine case, spilled catheter volume=1 ml and blood volume=5000 ml).

Using the safe upper limit set forth above (i.e., 0.5 units/ml) and the typical blood volume of 5000 ml, the nominal upper limit of 2500 units of heparin per ml in the catheter lock solution is obtained.

However, four factors militate in favor of a lower limit. First, patient blood volumes range as low as 3500 ml. Second, sometimes a practitioner inadvertently pushes the entire catheter volume of catheter lock solution into a patient. Third, hemodialysis patients have, as previously noted, a tendency to insufficient clotting. Fourth, the minimum heparin concentration for therapeutic anti-thrombotic effect is 0.2 units per ml in patients with a tendency to form clots. Accordingly, one preferred embodiment of the current invention carries an upper limit for heparin concentration of 1750 units heparin per ml. Another preferred embodiment carries an upper limit for heparin concentration of 1000 units heparin per ml. A third preferred embodiment carries an upper limit of 833 units heparin per ml. A fourth preferred embodiment has an upper limit of 583 units per ml, a highly preferred embodiment for the upper limit is 500 units per ml. Combining factors produces a most highly preferred embodiment of 150 units per ml. As will be appreciated by one skilled in the art, various concentrations of heparin up to 2500 units per ml can be safe for specific patients.

Some time after the tests referred to above were completed, an additional test specimen comprising the taurolidine formulation with a low concentration heparin (final concentration of about 125 units heparin per ml) was evaluated clinically in Germany. Work was undertaken at Dr. Sodemann's clinics to evaluate the taurolidine formulation modifications to determine if they might affect flow resistance. The modifications to the taurolidine locking solution included an increase in the pH, the addition of PVP to taurolidine, and the incorporation of minimal amounts of heparin (e.g., 125 units per ml) to the taurolidine based catheter lock solution.

Dr Sodemann was not able to observe any difference regarding flow resistance or any other clinical parameter. However, this observation was in the context that Dr. Sodemann had never seen a decrease in catheter patency using taurolidine-based locks as compared to high concentration heparin-based locks in the first place.

Clinical testing was then performed in French clinics on patients who had previously experienced flow resistance problems. In this group of patients it was observed that the addition of low concentration heparin reduced the need for flow resistance intervention, i.e., lysing, to low rates, comparable to those experienced with high concentration heparin lock solutions.

Subsequently other patients who had patency complications in Finland and Austria were tested with the taurolidine plus citrate locking solution with low concentration heparin added. In these cases also, an improvement over the original taurolidine formulation was noted and achieved patency rates similar to the patency rates patients for patients whose catheters were locked with high concentration heparin alone. In various experimental circumstances, concentrations of heparin as low as 50 units heparin per ml of catheter locking solution were found to have the beneficial effect of the current invention.

The taurinamide derivatives referred to are antimicrobial compounds which have been chemically described in earlier applications referenced above, which are incorporated by reference herein. The most preferred substance in this family is taurolidine. These compounds, condensation products of taurinamide and formaldehyde, are active not only against both gram-positive and grain-negative bacteria but also against exotoxins and endotoxins. For the purposes of this application these compounds are generically and collectively referred to as taurolidine.

The concentration of taurolidine in such solutions is preferably in the range of from about 0.4 to about 5% by weight, depending upon the solubility of the compound. Recent experiments have shown that addition of citrates and citric acid in combination, or alternatively the addition of citric acid and adjustment of the pH with sodium hydroxide, such that the pH of the end solution is in the vicinity of 5.2 to 6.5 substantially increases the biocidal effectiveness of taurolidine solution. The approach creates a buffer system of citric acid/sodium citrate by adjustment of pH using sodium hydroxide. This buffer system also resists changes in the pH due to the oxidation of formaldehyde to formic acid.

In addition, citric acid is a known antioxidant. Thus the use of citric acid and sodium citrate in this combination thus increases the stability and solubility of taurolidine in solution and prevents or severely slows down the precipitation out of solid taurolidine and reaction products frequently seen in taurolidine solution prepared with PVP. Long term stability tests have verified this result. The composition employed in the practice of the present invention preferably also contains a pharmacologically acceptable carrier solution, such as, water, Ringer's solution, or saline.

Other biologically acceptable acids and biologically acceptable salts thereof are possible for combination with taurolidine. Other possible such acids are acetic acid, dihydroacetic acid, benzoic acid, citric acid, sorbic acid, propionic acid, oxalic acid, fumaric acid, maleic acid, hydrochloric acid, malic acid, phosphoric acid, sulfurous acid, vanillic acid, tartaric acid, ascorbic acid, boric acid, lactic acid, ethylenediaminetetraacetic acid (EDTA), ethylene glycol-bis-{β-aminoethyl ether}-N,N,N',N'-tetraacetic acid, and diethylenetriamine pentaacetic acid, esters of p-hydroxybenzoic acid (Parabens), and the like, and biologically acceptable salts of the foregoing, such as, ammonium phosphate, potassium citrate, potassium metaphosphate, sodium acetate, sodium citrate, sodium lactate, sodium phosphate, and the like. A blood anticoagulating amount of an acid selected from the group consisting at citric acid, phosphoric acid, ethylenediaminetetraacetic acid (EDTA), ethylene glycol-bis-{β-aminoethyl ether}-N,N,N',N'-tetraacetic acid, and diethylenetriamine pentaacetic acid and biologically acceptable salts thereof is preferred. It is preferred that the acid employed in the practice of the present invention be an organic acid, especially one having at least one carboxyl group, particularly citric acid or EDTA. It is more preferred that the acid be citric acid and most preferred that it be used in combination with a citrate salt, e.g., sodium citrate, since, in addition to its pH lowering and anticoagulation capabilities, it is also known to be an antiseptic at the 3% level.

Since calcium is one factor that is known to have a role in the coagulation of blood, it is believed possible that at least part of EDTA's efficacy in anticoagulant activity may be brought about by this means. Sodium citrate is also believed to have anticoagulation properties by virtue at its ability to generate insoluble calcium citrate.

The acid and/or salt will be used in a concentration effective to bring about the desired volume anticoagulation effect and, at the same time, bring about, or help to bring about, an appropriate pH for biocidal effect. Heparin is added in low concentrations, preferably 50 units per ml to 150 units per mil. Typically, the combined antimicrobial, heparin and anticoagulant composition of the present invention will have a pH in the range of from about 3.0 to about 7, preferably from about 3.5 to about 6.5 and, most preferably from about 4.5 to about 6.5. Methods for adjusting the pH, familiar to those of skill in the art, can be employed. Where, as is preferred, trisodium citrate and citric acid are employed in the practice of the present invention, the trisodium citrate will typically be used in a concentration range of from about 5 to about 50 grams per liter. The citric acid will then be added in sufficient amount to bring the pH to the desired level. The formulation which is a preferred embodiment comprise about 1.35% Taurolidine, 4% citrate and acidic pH, generally in the range of 5 to 6.

Although the process of the present invention is primarily and preferably directed to maintaining the patency and asepsis of implanted hemodialysis catheters, beneficial effects may also be obtained in applying the process to other, similar, devices such as, central venous catheters, peripheral intravenous catheters, arterial catheters, Swan-Ganz catheters, umbilical catheters, percutaneous non-tunneled silicon catheters, cuffed tunnel central venous catheters as well as with subcutaneous central venous ports.

Various features and aspects of the present invention are illustrated further in the examples that follow. While these examples are presented to show one skilled in the art how to operate within the scope of the invention, they are not in any way to serve as a limitation upon the scope of the invention.

I claim:

1. A locking solution composition for treating and reducing infection and flow reduction in blood catheters, wherein the composition comprises a solution of:
   a. at least one taurinamide derivative; and
   b. heparin, in a concentration of 50-2500 units/ml (i) permit blood clotting within the blood catheter, and (ii) reduce taurinamide derivative-induced changes to the character of the clots.

2. The composition according to claim 1 wherein the taurinamide derivative is taurolidine.

3. The composition according to claim 1 further comprising a biologically acceptable acid and a biologically acceptable salt of said acid in a combination that brings the pH of the combination into a range that enhances antimicrobial activity of the taurinamide derivative.

4. The composition according to claim 3 wherein the biologically acceptable acid is chosen from the group consisting of citric acid and lactic acid and the biologically acceptable salt is chosen from the group consisting of citrate and lactate.

5. The composition according to claim 3 wherein the taurinamide derivative is taurolidine, the biologically acceptable acid is citric acid, the biologically acceptable salt is citrate, and the pH range is 5.2 to 6.5.

6. A locking solution composition for treating and reducing infection and flow reduction in blood catheters, wherein the composition comprises a solution of:
   a. at least one taurinamide derivative; and
   b. heparin, in a concentration of 50-2500 units/ml (i) permit blood clotting within the blood catheter, and (ii) reduce the formation of methemoglobin by the interaction of the at least one taurinamide derivative with blood.

7. The composition according to claim 6 wherein the taurinamide derivative is taurolidine.

8. The composition according to claim 6 further comprising a biologically acceptable acid and a biologically acceptable salt of said acid in a combination that brings the pH of the combination into a range that enhances antimicrobial activity of the taurinamide derivative.

9. The composition according to claim 8 wherein the biologically acceptable acid is chosen from the group consisting of citric acid and lactic acid and the biologically acceptable salt is chosen from the group consisting of citrate and lactate.

10. The composition according to claim 8 wherein the taurinamide derivative is taurolidine, the biologically acceptable acid is citric acid, the biologically acceptable salt is citrate, and the pH range is 5.2 to 6.5.

11. A locking solution composition for treating and reducing infection and flow reduction in blood catheters, wherein the composition comprises a solution of:
    a. at least one taurinamide derivative; and
    b. heparin, in a concentration of 50-2500 units/ml (i) permit blood clotting within the blood catheter, and (ii) reduce the formation of blood clots of the type which have a tendency to stick to catheter walls.

12. The composition according to claim 11 wherein the taurinamide derivative is taurolidine.

13. The composition according to claim 11 further comprising a biologically acceptable acid and a biologically acceptable salt of said acid in a combination that brings the pH of the combination into a range that enhances antimicrobial activity of the taurinamide derivative.

14. The composition according to claim 13 wherein the biologically acceptable acid is chosen from the group consisting of citric acid and lactic acid and the biologically acceptable salt is chosen from the group consisting of citrate and lactate.

15. The composition according to claim 13 wherein the taurinamide derivative is taurolidine, the biologically acceptable acid is citric acid, the biologically acceptable salt is citrate, and the pH range is 5.2 to 6.5.

16. A locking solution composition for reducing infection and flow reduction in blood catheters, wherein the locking solution composition comprises a solution of:
    a. at least one taurinamide derivative; and
    b. heparin, in a concentration of 50-2500 units/ml (i) permit blood clotting within the blood catheter, and (ii) reduce fragmentation and adherence of clots and clot fragments to the wall of the blood catheter, thereby enhancing removal of clots and clot fragments during preparation of the catheter for use.

17. The composition according to claim 16 wherein the taurinamide derivative is taurolidine.

18. The composition according to claim 16 further comprising a biologically acceptable acid and a biologically acceptable salt of said acid in a combination that brings the pH of the combination into a range that enhances antimicrobial activity of the taurinamide derivative.

19. The composition according to claim 18 wherein the biologically acceptable acid is chosen from the group consisting of citric acid and lactic acid and the biologically acceptable salt is chosen from the group consisting of citrate and lactate.

20. The composition according to claim 18 wherein the taurinamide derivative is taurolidine, the biologically acceptable acid is citric acid, the biologically acceptable salt is citrate, and the pH range is 5.2 to 6.5.

* * * * *